United States Patent
Kuhn et al.

(10) Patent No.: US 8,275,432 B2
(45) Date of Patent: Sep. 25, 2012

(54) IMPLANTABLE OPTICAL SENSOR AND METHOD FOR MANUFACTURE

(75) Inventors: Jonathan L. Kuhn, Ham Lake, MN (US); Timothy J. Davis, Coon Rapids, MN (US); Can Cinbis, Shoreview, MN (US); Robert M. Ecker, Lino Lakes, MN (US); Shawn D. Knowles, Princeton, NJ (US); Thomas A. Anderson, New Hope, MN (US); Jeffrey M. Jelen, New Hope, MN (US)

(73) Assignee: Medtronic, Inc., Minneapolis, MN (US)

( * ) Notice: Subject to any disclaimer, the term of this patent is extended or adjusted under 35 U.S.C. 154(b) by 1321 days.

(21) Appl. No.: 11/955,056

(22) Filed: Dec. 12, 2007

(65) Prior Publication Data

US 2009/0156912 A1 Jun. 18, 2009

(51) Int. Cl.
*A61B 5/1455* (2006.01)

(52) U.S. Cl. ......... 600/310; 600/316; 600/322; 600/323

(58) Field of Classification Search ............... 600/310, 600/322–327, 333, 339, 341, 316; 438/65; 257/85, E31.001
See application file for complete search history.

(56) References Cited

U.S. PATENT DOCUMENTS

| | | | |
|---|---|---|---|
| 4,202,339 A | | 5/1980 | Wirtzfeld et al. |
| 4,275,404 A | * | 6/1981 | Cassiday et al. ............. 257/85 |
| 4,467,807 A | | 8/1984 | Bornzin |
| 4,730,389 A | | 3/1988 | Baudino et al. |
| 4,825,872 A | * | 5/1989 | Tan et al. ................. 600/344 |
| 4,938,218 A | * | 7/1990 | Goodman et al. ......... 600/338 |
| 5,054,488 A | * | 10/1991 | Muz ........................ 600/344 |
| 5,823,951 A | * | 10/1998 | Messerschmidt ............ 600/322 |
| 5,902,326 A | | 5/1999 | Lessar et al. |
| 5,917,167 A | * | 6/1999 | Bestel ........................ 218/138 |
| 6,125,290 A | | 9/2000 | Miesel et al. |
| 6,125,291 A | * | 9/2000 | Miesel et al. ................ 600/333 |
| 6,134,459 A | * | 10/2000 | Roberts et al. .............. 600/333 |
| 6,144,866 A | | 11/2000 | Miesel et al. |
| 6,198,952 B1 | | 3/2001 | Miesel et al. |
| 6,330,464 B1 | * | 12/2001 | Colvin et al. ................ 600/341 |
| 6,661,167 B2 | | 12/2003 | Eliashevich et al. |
| 6,711,423 B2 | | 3/2004 | Colvin |
| 7,152,977 B2 | | 12/2006 | Ruda et al. |
| 7,167,309 B2 | | 1/2007 | Saxena et al. |
| 2004/0197267 A1 | | 10/2004 | Black et al. |
| 2004/0246744 A1 | | 12/2004 | Krupa et al. |
| 2005/0006651 A1 | | 1/2005 | LeBoeuf et al. |
| 2006/0255353 A1 | | 11/2006 | Taskar et al. |

OTHER PUBLICATIONS

International Search Report, PCT/US2008/084675, Feb. 23, 2009, 7 Pages.

* cited by examiner

*Primary Examiner* — Eric Winakur
*Assistant Examiner* — Chu Chuan (JJ) Liu
(74) *Attorney, Agent, or Firm* — Evans M. Mburu; Michael C. Soldner

(57) ABSTRACT

An implantable optical sensor and associated manufacturing method include a sensor housing having an inner surface and an outer surface and a window formed in the housing extending between the housing inner surface and the housing outer surface. An opto-electronic device enclosed within the housing and having a photonic surface is operatively positioned proximate the window for emitting light through the window or detecting light through the window. An optical coupling member is positioned between the opto-electronic device and the window for reducing light reflection at a surface within the implantable optical sensor.

39 Claims, 15 Drawing Sheets

US 8,275,432 B2

IMPLANTABLE OPTICAL SENSOR AND METHOD FOR MANUFACTURE

REFERENCE TO RELATED APPLICATIONS

Cross-reference is hereby made to co-pending U.S. patent application Ser. No. 11/955,025, now published as U.S. Publication No. 2009/0156918, entitled "IMPLANTABLE OPTICAL SENSOR AND METHOD FOR USE" and U.S. patent application Ser. No. 11/955,039, now abandoned, entitled "IMPLANTABLE OPTICAL SENSOR AND METHOD FOR MANUFACTURE", both applications filed on even date herewith and incorporated herein by reference in their entirety.

TECHNICAL FIELD

The invention relates generally to implantable medical devices and, in particular, to an implantable optical sensor.

BACKGROUND

Implantable medical devices (IMDs) for monitoring a physiological condition or delivering a therapy include one or more physiological sensors. Physiological sensors used in conjunction with an IMD provide a signal related to a physiological condition from which a patient state or the need for a therapy can be assessed. Examples of such IMDs include heart monitors, pacemakers, implantable cardioverter defibrillators (ICDs), myostimulators, neurological stimulators, drug delivery devices, insulin pumps, glucose monitors, etc.

Optical sensors are employed in IMDs as physiological sensors configured to detect changes in light modulation by a body fluid or tissue measurement volume due to a change in a physiological condition in the body fluid or tissue. Such optical sensors can be used, for example, for detecting changes in metabolite levels in the blood, such as oxygen saturation levels or glucose level, or changes in tissue perfusion. Monitoring such physiological conditions provides useful diagnostic measures and can be used in managing therapies for treating a medical condition. For example, a decrease in blood oxygen saturation or in tissue perfusion may be associated with insufficient cardiac output or respiratory function. Thus monitoring such signals allows an implantable medical device to respond to a decrease in oxygen saturation or tissue perfusion, for example by delivering electrical stimulation therapies to the heart to restore a normal hemodynamic function. One example of an implantable optical sensor used for monitoring blood oxygen saturation is generally disclosed in commonly assigned U.S. Pat. No. 6,198,952 (Miesel), hereby incorporated herein by reference in its entirety. Cardiac pacemakers that respond to changes in blood oxygen saturation as measured by an optical sensor are generally disclosed in U.S. Pat. No. 4,202,339 (Wirtzfeld) and in U.S. Pat. No. 4,467,807 (Bornzin), both of which patents are incorporated herein by reference in their entirety.

Implantable optical sensors typically include a set of light emitting diodes (LEDs), for example two or more LEDs, each emitting a different narrow band of light, and a photodetector for detecting emitted light that is scattered by body fluid or tissue back to the sensor. A current signal emitted by the photodetector in response to the scattered light incident on the photodetector is correlated to a physiological change in the adjacent body fluid or tissue. It is generally desirable to provide sensitive light detection to achieve reliable measurements and to minimize the size of such implantable sensors to minimize patient discomfort and to facilitate the ease of implantation procedures.

DETAILED DESCRIPTION

Figure 1:
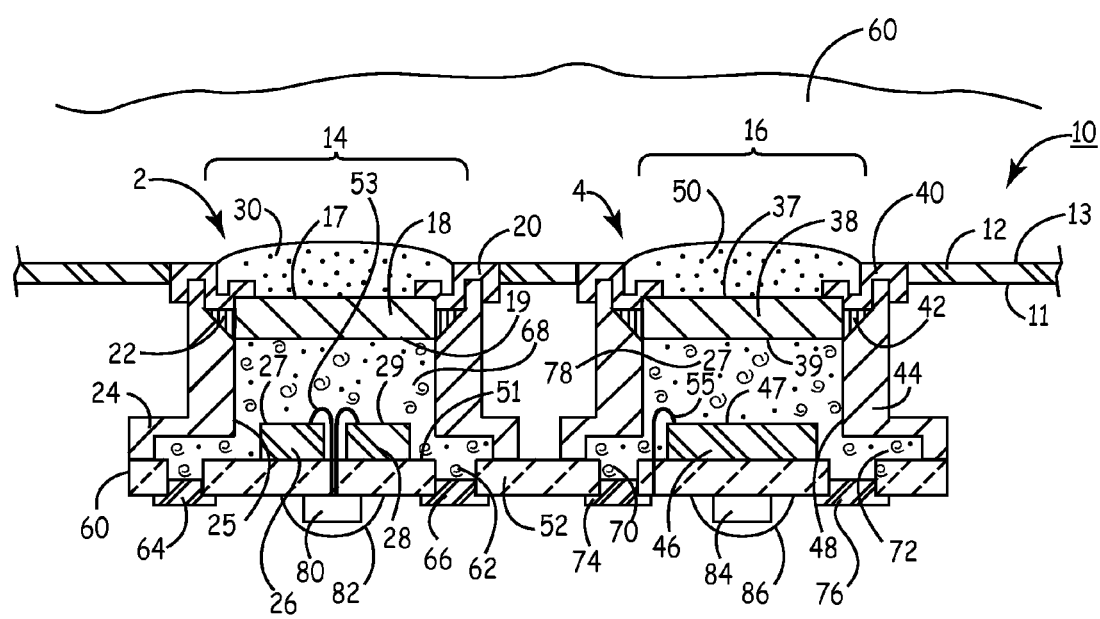
FIG. 1 is a side sectional view of an optical sensor according to one embodiment of the invention.

In the following description, references are made to illustrative embodiments for carrying out the invention. It is understood that other embodiments may be utilized without departing from the scope of the invention. For purposes of clarity, the same reference numbers are used in the drawings to identify similar elements. The term "optical," as used herein with regard to a sensor material or component, refers to a material or component that is substantially transparent, at least to the light wavelengths of interest being emitted or detected by the sensor. As used herein, the term "photoemitting device", also referred to herein as a "light emitting device", refers to any opto-electronic device capable of emitting light, including for example LEDs and vertical cavity surface emitting lasers (VCSELs). The term "photodetector", also referred herein to as "photodetecting device" and "light detecting device," refers to any opto-electronic device capable of emitting current in the presence of light, including for example photoresistors or light dependent resistors, photodiodes, phototransistors, photovoltaic cells, or charge-coupled devices.

FIG. 1 is a side sectional view of an optical sensor 10 according to one embodiment of the invention. Sensor 10 may be incorporated in the housing of an implantable medical device, such as in a subcutaneously implanted hemodynamic monitor, pacemaker or ICD housing, or carried by a medical electrical lead. Sensor 10 includes a light emitting portion 14, a light detecting portion 16, and a capsule or housing 12 for enclosing optical sensor components. Housing 12 is typically hermetically sealed to protect against damage to internal sensor components due to the ingress of body fluids. Each portion 14 and 16 includes a window 2 and 4, respectively, formed in openings in the housing 12 for passing emitted light out from light emitting portion 14 and passing scattered light into the light detecting portion 16. Windows 2 and 4 each extend between a housing inner surface 11 and a housing outer surface 13.

Windows 2 and 4 each include an optical lens 18 and 38, commonly formed from sapphire or glass. As used herein, the term "lens" refers to an optical structure through which emitted and scattered light travels through without necessarily being focused. As such, lenses 18 and 38 are not provided as convex or concave structures for focusing light but merely serve to cover windows 2 and 4 to protect internal sensor components while allowing light to pass through windows 2 and 4. Lenses 18 and 38 are mounted within respective openings formed in housing 12 in a manner that maintains the hermeticity of housing 12. In one embodiment, lenses 18 and 38 are hermetically sealed within respective openings in housing 12 using ferrules 20 and 40.

Ferrules 20 and 40 are bonded to lenses 18 and 38 at joints 22 and 42. Joints 22 and 42 may be gold brazed joints, welded joints or formed using a polymer adhesive depending on the ferrule material and other manufacturing processes used in fabricating sensor 10. Housing 12 may be formed, for example, from titanium, stainless steel, ceramic, glass, or a rigid polymer. In one embodiment, housing 12 and ferrules 20 and 40 are each formed from titanium. Ferrules 20 and 40 are then welded within openings formed in housing 12 to maintain hermeticity of sensor 10. The optical window assembly generally disclosed in U.S. Pat. No. 5,902,326 (Lessar, et al.), hereby incorporated herein by reference in its entirety, may be implemented in embodiments of the present invention.

Windows 2 and 4 may further include transparent polymeric seals 30 and 50 formed over lenses 18 and 38 and ferrules 20 and 40, respectively. Seals 30 and 50 may be formed, for example, from silicone rubber and, along with lenses 18 and 38 form windows 2 and 4 through which emitted and scattered light travels. Seals 30 and 50 protect gold braze joints 22 and 42 from the corrosive effects of bodily fluids and provide a smooth, convex surface that reduces the susceptibility of sensor 10 to blood clot formation and excessive tissue encapsulation over lenses 18 and 38. Blood clot formation and tissue encapsulation reduces light transmission into and out of sensor 10.

The emitting portion 14 includes opto-electronic devices for emitting light, shown as LEDs 26 and 28. LEDs 26 and 28 are mounted on a substrate, embodied as a printed circuit board 52 in FIG. 1, to enable the necessary connections for applying a voltage to each of LEDs 26 and 28 to cause light emission at appropriate times. An enclosure 24 surrounds and encloses the LEDs 26 and 28 to prevent scattering of light and promote transmission of light through lens 18. Enclosure 24 may be formed from a rigid, non-transparent material, such as liquid crystal polymer. Alternatively, enclosure 24 can be formed from other non-transparent materials, for example a non-rigid polymer material, such as silicone, formed as a molded component. Enclosure 24 is coupled to circuit board 52 and extends to window 2 where enclosure 24 may be coupled to housing 12 via ferrule 20 and bonded to lens 18 at joint 22. Enclosure 24 may be coupled to circuit board 52 using a hard die coat dam holding wall 24 to the board 52. In embodiments implementing sensor 10 as a lead-based sensor, enclosure 24 is optional with housing 12 enclosing sensor components in a sensor "capsule" carried by a lead body.

The two LEDs 26 and 28 typically emit light corresponding to two different wavelengths or colors. In one embodiment, in which sensor 10 is used for sensing blood oxygen saturation, one of LEDs 26 and 28 emits red light and the other emits infrared light. In another embodiment, in which sensor assembly 10 is used for sensing tissue perfusion, a third LED may be included. Emitted light passes through lens 18 and enters body fluid or tissue volume 60. It is recognized that one or more LEDs may be included in light emitting portion 14 having selected light wavelength emission properties. The number of LEDs and corresponding emission wavelengths will be selected according to the requirements of a particular application and will depend on the physiological condition being monitored.

The detecting portion 16 includes one or more photodetectors 46. Photodetector 46 is mounted on printed circuit board 52 to enable appropriate electrical connections between photodetector 46 and an integrated circuit 84 including circuitry for maintaining a proper bias of photodetector 46 and carrying light-induced signals from photodetector 46. An enclosure 44 surrounds the photodetector 46 to promote light traveling through lens 38 to fall on a photonic surface 47 of photodetector 46 and prevent scattered light from light emitting portion 14 from reaching photodetector 46 directly. Enclosure 44 may share a common side with enclosure 24 in some embodiments and may be formed using methods and materials as described above with regard to enclosure 24.

Light emitted from emitting portion 14 is scattered by the body fluid or tissue volume 60. A portion of the scattered light travels through window 4 to photodetector 46. Light modulation due to a physiological change in the body fluid/tissue volume 60 results in a signal generated by the photodetector 46 that is correlated to the changing physiological condition. In an optical sensor for estimating oxygen saturation in body fluid or tissue volume 60 that includes a red LED and an infrared LED in emitting portion 14, the intensity of red light scattered by the body fluid or tissue volume 60 and detected by photodetector 46 is dependent on the concentration of oxygen in the body fluid or tissue volume 60. The intensity of infrared light scattered by the body fluid or tissue volume 60 can be made independent of the concentration of oxygen by proper choice of infrared wavelength. The intensity of scattered red light detected by the photodetector 46 is normalized by the intensity of scattered infrared light to minimize the effect of variables such as tissue overgrowth, hematocrit and blood flow velocity.

Circuit board 52 is shown as a single circuit board on which both emitting portion 14 and detecting portion 16 are assembled. In alternative embodiments, separate circuit boards may be provided for each emitting and detecting portion. Integrated circuits 80 and 84 are provided on the back side of the circuit board 52 for electrically coupling to LEDs 26 and 28 and photodetector 46, respectively. Electrical coupling is shown schematically by conductors 53 in light emitting portion 14 and conductor 55 in light detecting portion 16.

Conductors 53 and 55 may represent wire bonds between the opto-electronic devices 26, 28 and 46 and traces printed on circuit board 52. Circuits 80 and 84 include capacitors, resistors, etc. for carrying activation signals to LEDs 26 and 28 and carrying current signals generated by photodetector 46 in response to scattered light incident on photodetector 46 and providing the signal to processing circuitry configured to perform an algorithm for detecting a change in a physiological condition using the current signal. Integrated circuit 84 may include an analog-to-digital converter and flash memory for digitizing the analog signal and providing the digitized signal to processing circuitry. Each of circuits 80 and 84 are optionally embedded in an insulative coating material 82 and 86, respectively, to protect the circuitry therein. Coatings 82 and 86 are typically a hard die coating that minimizes light exposure to the integrated circuits 80 and 84.

In various embodiments of the invention, light-emitting portion 14 includes an optical coupling member positioned between LEDs 26 and 28 and window 2, and/or light detecting portion 16 includes an optical coupling member positioned between photodetector 46 and window 4. In one embodiment, light-emitting portion enclosure 24 is filled with an optical polymer material forming optical coupling member 68 for reducing the reflection of emitted light at component interfaces within light emitting portion 14. More specifically, member 68 is formed from a material having a high refractive index, also referred to herein as "index of refraction", for optically coupling LEDs 26 and 28 with lens 18 in order to reduce the reflection of emitted light as light leaves the photonic surfaces 27 and 29 of LEDs 26 and 28, respectively, as compared to light reflected at the photonic surfaces 27 and 29 when interfaced with air. Member 68 may also be embodied to reduce reflections of emitted light at the inner surface 19 of lens 18 as compared to reflections that would otherwise occur at a lens inner surface-air interface.

Materials suitable for forming member 68 have a refractive index of about 1.5 or higher. The nominal optimal value of the refractive index of member 68 is the square root of the product of the refractive indices of the lenses 26 and 28 and LED material. However, due to the very high absorption of the LED material, an even higher index is desirable. The refractive index of a lens 18 formed from sapphire is about 1.7. The refractive index of LEDs 26 and 28 when formed from gallium arsenide is about 3.9. As such, member 68 would optimally be formed from materials having a refractive index of 2.6 or even greater. The practical limit of the refractive index for commercially available polymer materials is roughly 1.7 at red to near infrared wavelengths.

As such, practical examples of suitable materials for forming member 68 from currently available materials include thermoset, elastomer, adhesive, epoxy, silicone, thermoset varnish, acrylic, ester, and thixotropic gel materials. Materials may be two part materials that are mixed at the time of forming member 68. Among numerous possible materials for forming member 68 are: LS 6257, a two-part thermoset available from Nusil Technology, Wareham, Mass.; C-imide HR742, a thermoset varnish available from Optmate, Osaka, Japan; Abelux® A4021T, an adhesive available from Ablestik, Rancho Dominguez, Calif.; and SL-1259, a thixotropic gel, available from Nusil. Other considerations taken when selecting a material used to form member 68 include viscosity of the material prior to cure, curing methods, and the effects of aging on optical properties.

In past practice, LEDs included in a light emitting portion of an implantable optical sensor interfaced with air in the space between the LEDs 26 and 28 and the window 2. As such, considerable light reflections occurring at the LED-air interface and at the air-lens interface reduce the overall efficiency of light emission. By providing an optical coupling member 68, light extraction from LEDs 26 and 28 at photonic surfaces 27 and 29, respectively, is increased and the extracted light is coupled from the LEDs 26 and 28 directly to lens 18. As such, light emission becomes more efficient such that sensor power requirements are reduced and/or the depth of light penetration into an adjacent body fluid or tissue volume 60 is increased.

In the embodiment shown, member 68 completely fills the space within enclosure 24 not occupied by LEDs 26 and 28 or other components. Member 68 may be formed after assembling enclosure 24 with circuit board 52 and ferrule 20, lens 18 and housing 12 by injecting a selected material through a fill port 60 provided in circuit board 52. An overfill port 62 may be provided to facilitate complete filling of enclosure 24 and removal of air bubbles during filling and curing processes. Ports 60 and 62 may be covered with opaque caps 64 and 66 to prevent light leakage. Caps 64 may be solid members inserted over ports 60 and 62 or may be applied as a coating. In some embodiments coating material 82 and 86 may extend over ports 60, 62 and 70, 72, respectively, thereby replacing caps 64, 66, 74 and 76.

In high voltage therapy applications, where the can is biased to a high voltage relative to the internal circuitry, member 68 provides electrical insulation of conductors 53 allowing LEDS 26 and 28 to be positioned closer to housing inner surface 11 and window 2, further increasing optical efficiency. For example, with a therapy voltage of greater than a few hundred volts, a safe standoff distance of over 50 mils may be required between the housing inner surface 11 and the circuit board 52 to prevent electrical breakdown. If the conductors 53 are covered by an optical coupling material that additionally provides electrical insulation between the conductors and housing 12, the standoff distance may be reduced from over 50 mils to approximately 15 mils or less, for example. It is recognized that this example is illustrative, and in other implantable medical devices these distances may vary, but, overall, may be reduced when an optical coupling member provides electrical insulation to the opto-electronic device and associated electrical connections to a substrate-mounted integrated circuit.

An optical coupling member 78 may also be included in light detecting portion 16. Member 78 may be formed in a similar manner as member 68 such that member 78 completely fills space within enclosure 44 not occupied by photodetector 46 or other components. The material used to form member 78 can be injected through port 70 formed in circuit board 52 with excess material and air bubbles escaping through overfill port 72. Caps 74 and 76 are positioned over ports 70 and 72 after filling to prevent light loss. Materials appropriate for forming coupling member 78 correspond to those listed above for member 68. Member 78 reduces light reflections that would otherwise occur at a lens inner surface-air interface and at a photonic surface-air interface as light scattered by body fluid/tissue volume 60 travels through window 4 to photodetector 46. The nominal optimal refractive index of member 78 would be approximately 2.5 for a sapphire lens 38 and bare silicone photodetector 46. The practical limit for commercially available polymer materials is roughly 1.7. As such, member 78 may be formed from a material having a refractive index of about 1.5 to 1.7.

Prior to forming members 68 and 78 within enclosures 24 and 44, the inner surfaces 25 and 48 of enclosures 24 and 44, respectively, and circuit board 52 may be treated to promote adhesion between members 68 and 78 and the inner surfaces 25 and 48, respectively, and top side 51 of circuit board 52.

Such treatment generally includes cleaning and may include applying a coating over inner surfaces 25 and 48 and circuit board top side 51. Among the appropriate coatings for promoting adhesion are surfactants or primers such as NuSil Technology LS-3200-10 Series Optical Primer.

In some embodiments, seals 30 and 50 are formed from an optical polymer having a refractive index selected to reduce reflections of light at the outer surface 17 of lens 18 and the outer surface 37 of lens 38, respectively. For example, if adjacent tissue volume has a refractive index of approximately 1.4 and lens 18 has a refractive index of 1.7, the optical polymer used to form seal 30 may be selected having a refractive index of approximately 1.5.

Figure 2:
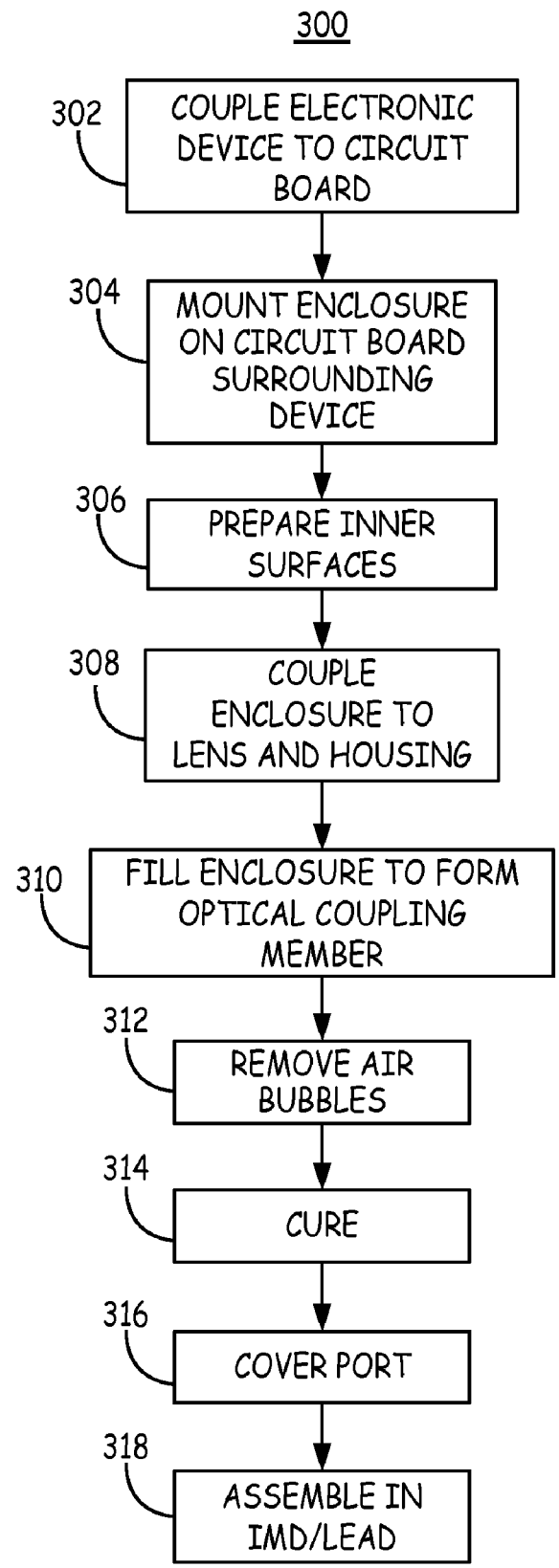
FIG. 2 is a flow chart of one method for manufacturing an implantable optical sensor, such as the sensor shown in FIG. 1.

FIG. 2 is a flow chart of a method for manufacturing an implantable optical sensor, such as sensor 10 shown in FIG. 1, according to one embodiment of the invention. Method 300 generally applies to methods for manufacturing both light emitting and light detecting portions of an implantable optical sensor. Method 300 includes coupling an opto-electronic device configured for emitting or detecting light to a circuit board or other substrate that facilitates electrical coupling to the opto-electronic device at block 302. Electrical connections between the opto-electronic device and an integrated circuit may be made, for example, using wire bonds. At block 304, an enclosure is mounted onto the circuit board surrounding the opto-electronic device. At block 306, inner surfaces of the enclosure and the circuit board are cleaned and may be coated for promoting adhesion of an optical coupling member material to the interior surfaces of the sensor. At block 308, the enclosure is coupled to a sensor housing and/or to a lens positioned in a window formed in the housing. For example, the enclosure may be coupled to a window lens and the sensor housing via a ferrule as shown in FIG. 1. In other embodiments, the enclosure may be coupled directly to the inner surface of the housing.

At block 310, the enclosure is at least partially filled by injecting a material into the enclosure via a fill port, e.g. a port formed in the circuit board or substrate upon which the opto-electronic device is mounted. Prior to curing, the sensor may be placed in a centrifuge or vacuum for removing air bubbles from the material at block 312. The material is cured at block 314 thereby forming an optical coupling member positioned between the opto-electronic device and the window of the optical sensor. Depending on the material chosen for forming the optical coupling member, the curing process may include heating, applying pressure, applying ultraviolet light, or curing at room temperature. After curing, the fill port used to inject the material into the enclosure is covered at block 316 with an opaque cap or coating to prevent light losses.

At block 318, the sensor is assembled in an IMD or medical electrical lead for use as an implantable optical sensor. In part, the sensor is electrically coupled to conductors and/or connector elements to enable electrical coupling to a sensor module that includes sensor driver circuitry and sensor signal processing circuitry. The sensor may be positioned along a medical electrical lead body or incorporated in or on the housing of an IMD.

Figure 3:
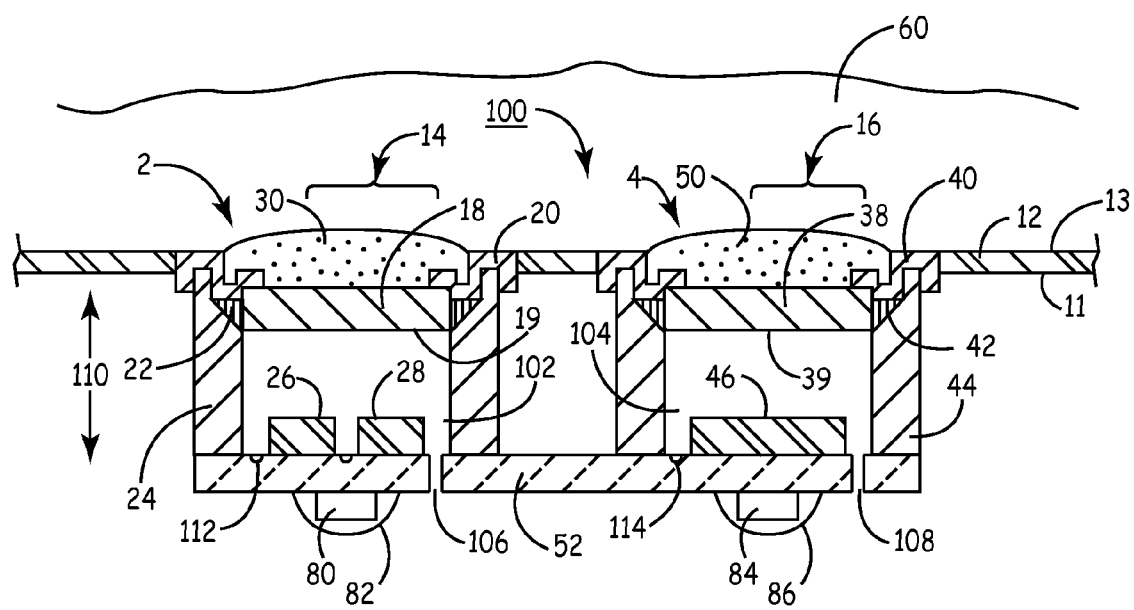
FIG. 3 is a side sectional view of an alternative embodiment of an optical sensor including an optical coupling member.

FIG. 3 is a side sectional view of an alternative embodiment of an optical sensor including an optical coupling member. Elements indicated by identical reference numerals in FIG. 3 correspond to like-numbered elements shown in FIG. 1. Sensor 100 includes light emitting portion 14 and light detecting portion 16 as generally described above. Emitting portion 14 may include an optical coupling member 102 positioned between window 2 and LEDs 26 and 28. Detecting port 16 may include optical coupling member 104 positioned between window 4 and photodetector 46. In this embodiment, members 102 and 104 are formed from a material having a high index of refraction, e.g. greater than about 1.5 and having a coefficient of thermal expansion less than the coefficient of thermal expansion of enclosures 24 and 44. For example, in one embodiment, optical coupling members 102 and 104 are formed from materials having different coefficients of thermal expansion than the material used to form enclosures 24 and 44 such that the relative shrinkage of the enclosures 24 and 44 upon cooling from an elevated temperature will be about 0.5% to 5% greater than the shrinkage of optical members 102 and 104.

After assembling the LEDs 26 and 28 and enclosure 24 onto circuit board 52, enclosure 24 is filled with an optical polymer material selected for forming member 102. The enclosure 24 is then assembled with the ferrule 20 and lens 18. The entire assembly is then heated to a high temperature to cure the optical polymer material. As the assembly cools from the high temperature, the optical polymer material becomes compressed within enclosure 24 due to the mismatch of the coefficients of thermal expansion of the polymer and the enclosure. The enclosure 24, having a higher coefficient of thermal expansion, will shrink more than the member 102 upon cooling. The enclosure 24 is designed such that the shrinkage associated with the coefficient of thermal expansion occurs preferentially in the direction of the height 110 of enclosure 24. The compressed optical material results in member 102 forming a compression or interference fit between the lens inner surface 19 and the LEDs 26 and 28, thereby reducing reflections that would otherwise occur at the surface of the LEDs 26 and 28 and at the lens inner surface 19.

Likewise, an optical coupling member 104 may be formed in light detecting portion 16 by filling enclosure 44 with an optical polymer having a lower coefficient of thermal expansion than enclosure 44. Upon cooling from a curing temperature greater than room temperature, member 104 becomes compressed by enclosure 44, thereby forming a compression or interference fit with lens inner surface 39 and photodetector 46 to diminish reflections that otherwise occur at those surfaces.

Circuit board 52 may optionally be provided with ports 106 and 108 that may be used as overfill ports during injection of the optical material into enclosures 124 and 144. Filling may be performed prior to or after coupling enclosures 124 and 144 to ferrules 20 and 40 and lenses 18 and 38, respectively. When filling is performed after coupling the enclosures to the ferrules and lenses, a fill port and an overfill port may be provided in each of emitting portion 14 and detecting portion 16 as generally shown in FIG. 1.

Emitting portion 14 and detecting portion 16 are further provided with pressure relief features to prevent excess pressure within each portion 14 and 16 upon compression of members 102 and 104. In one embodiment, pressure relief features are provided as grooves 112 and 114 which member 102 can become pressed into during cooling and compression of member 102. Pressure relief features may alternatively be embodied as any depression, channel, groove or other relief feature formed along any interior surface within emitting portion 14 and detecting portion 16.

Figure 4:
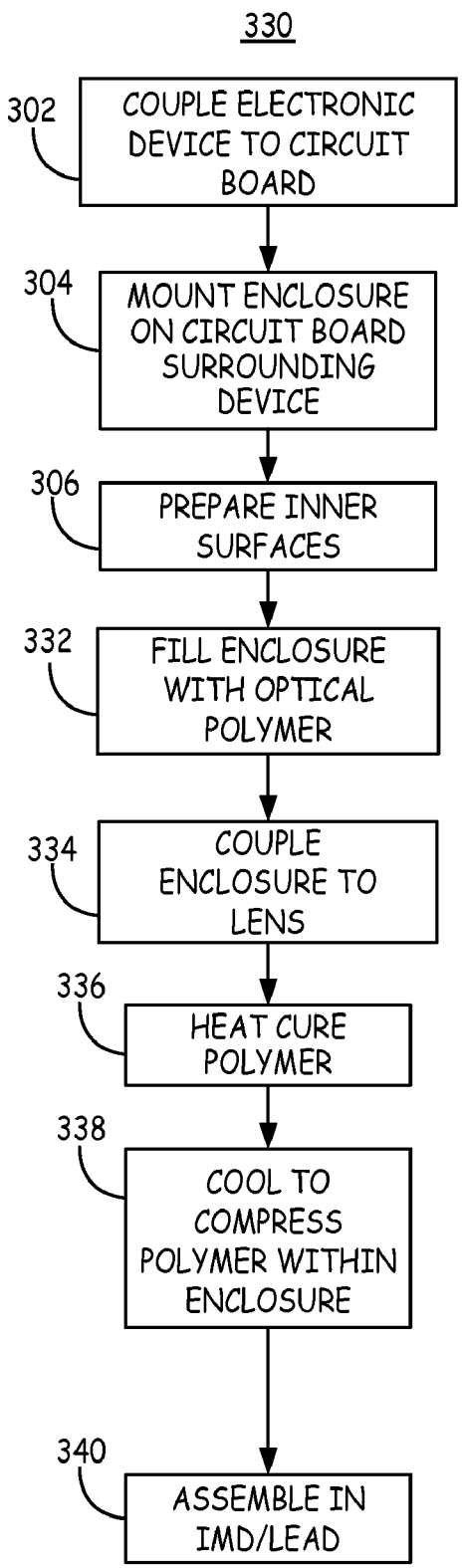
FIG. 4 is a flow chart of one method for manufacturing an optical sensor having a compressed optical coupling member.

FIG. 4 is a flow chart of one method 330 for manufacturing an optical sensor having a compressed optical coupling member. Blocks 302 through 306 correspond to identically-numbered blocks shown in FIG. 2. At block 302, an opto-electronic device is mounted on a circuit board for either emitting or detecting light within the optical sensor. An enclosure is mounted on the circuit board surrounding the opto-electronic device at block 304. At block 306, inner surfaces of the enclosure and circuit board may be cleaned to promote better adhesion of an optical polymer introduced into the enclosure. The inner surfaces may also be coated or otherwise treated in a manner that promotes adhesion to the optical polymer.

At block 332, the enclosure is filled with an optical polymer selected to have a high index of refraction, for example greater than 1.5, and a coefficient of thermal expansion lower than the enclosure material. After filling, the enclosure is coupled to the lens, at block 334, for example using a ferrule as shown in FIG. 3. At block 336, the assembly including the enclosure, circuit board with the opto-electronic device mounted thereon, and lens, all of which form an interior space filled with the optical polymer, is heated to cure the optical polymer. At block 338, the assembly is allowed to cool. During cooling the enclosure shrinks in height more than the optical polymer thereby forming an optical coupling member positioned between the lens inner surface and the opto-electronic device and having an interference or compression fit therebetween.

At block 340, the sensor is assembled in an IMD or medical electrical lead for use as an implantable optical sensor as described previously in conjunction with FIG. 2.

Figure 5A:
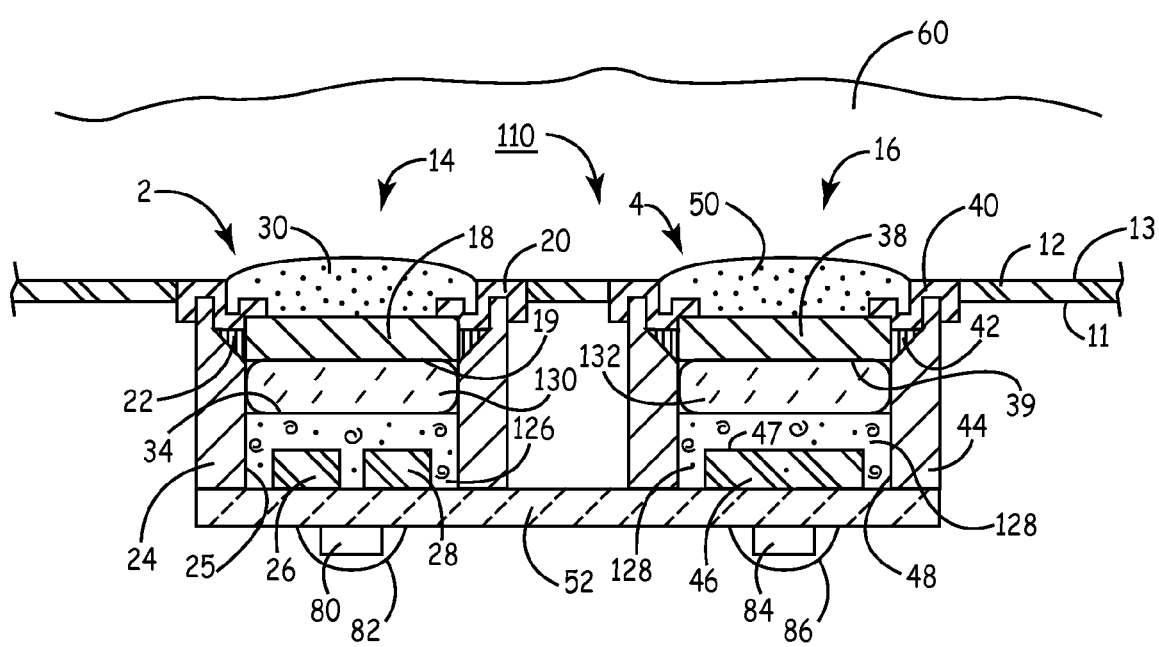
FIG. 5A is a side sectional view of yet another embodiment of an implantable optical sensor including an optical coupling member.

FIG. 5A is a side sectional view of yet another embodiment of an implantable optical sensor including an optical coupling member. As in FIG. 3, identically-numbered elements correspond to those shown in FIG. 1. In sensor 110, an optical coupling member positioned in the light emitting portion 14 includes a first portion 126 and a second portion 130. The first coupling member portion 126 is formed by partially filling enclosure 24 with an optical polymer material after mounting enclosure 24 to circuit board 52 surrounding LEDs 26 and 28. First coupling member portion 126 is formed from an optical polymer having a high index of refraction to reduce reflections that otherwise occur at the surface of LEDs 26 and 28.

The second coupling member portion 130 is a preformed, resilient member that is positioned over the first coupling member portion 126. Second coupling member portion 130 is sized to form an interference or compression fit between the lens inner surface 19 and the top surface 134 of first coupling member portion 126 after assembling enclosure 24 with ferrule 20 and lens 18. The first coupling member portion 126 may be formed of a material having higher durometer than the second coupling member portion such that the second coupling member portion becomes slightly compressed within enclosure 24, between lens 18 and first coupling member portion 126.

Second coupling member portion 130 may be formed with an outer diameter somewhat smaller than the diameter of enclosure inner surface 25 such that second coupling member 130 may expand radially as it is compressed between lens 18 and first coupling member portion 126. Alternatively, enclosure 24 may be formed with pressure relief features, e.g. grooves or channels as described above, for receiving member 130 as it is compressed between lens 18 and first coupling member portion 126.

Second coupling member portion 130 reduces reflections that otherwise occur at lens inner surface 19. The first and second coupling member portions 130 and 126 are formed from materials having similar or matched indices of refraction to minimize reflections that occur at the interface between first and second coupling members 130 and 126. In one embodiment, first coupling member portion 126 is formed from NOA 60, a UV curable ester available from Norland (Cranbury, N.J.) having a durometer of 81 Shore D and refractive index of 1.56 and second coupling member portion 130 is formed from LS 3357, a two part thermoset available from Nusil Technology having a durometer of 15 Shore A and refractive index of 1.57. In alternative embodiments, rather than being a preformed member, second coupling member portion 130 may be formed of a no-cure optical gel, such as SL-1259 thixiotropic gel available from Nusil Technology.

Light detecting portion 16 may likewise include a two-part optical coupling member formed from a first portion 128 formed by partially filling enclosure 44 with an optical polymer material and a second, pre-formed portion 132 positioned between the first portion 128 and lens 38 in the same or similar manner as described above. The first portion 128 reduces reflections that otherwise occur at the photonic surface 47 of photodetector 46, and the second portion 132 reduces reflections that otherwise occur at lens inner surface 39. The first and second optical coupling member portions 128 and 132 have similar or matched indices of refraction to minimize reflections occurring between the first and second portions 128 and 132.

Figure 5B:
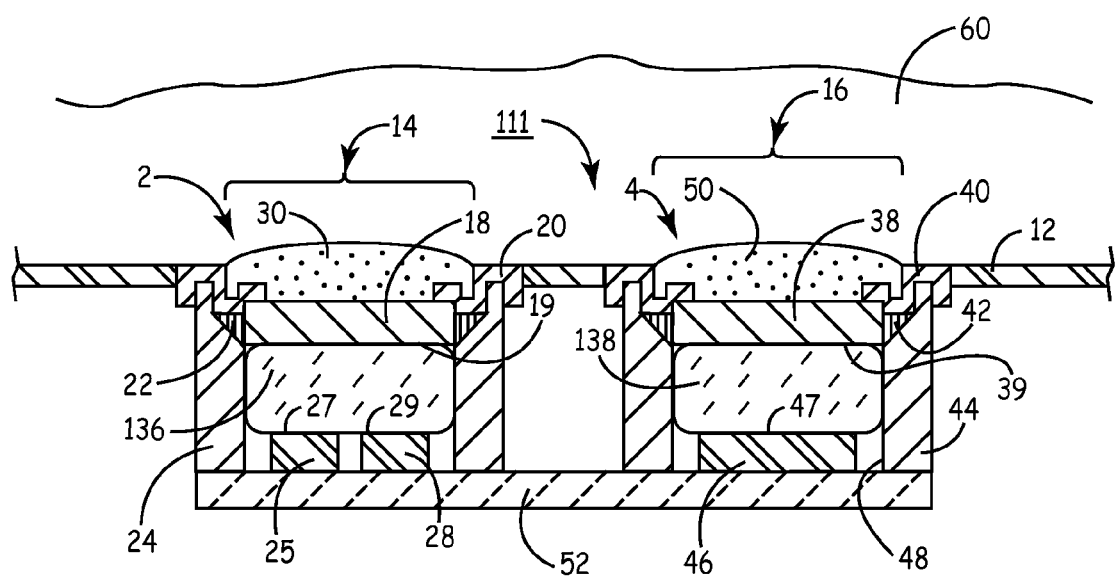
FIG. 5B is a side sectional view of an implantable optical sensor including a preformed optical coupling member.

FIG. 5B is a side sectional view of an implantable optical sensor including a preformed optical coupling member. In sensor 111, a preformed optical coupling member 136 is positioned in light emitting portion 14 between, and in direct contact with, photonic surfaces 27 and 29 of LEDs 26 and 28 and lens inner surface 19. In light detecting portion 16, a preformed optical coupling member 138 is positioned between, and in direct contact with, photonic surface 47 of photodetector 46 and lens inner surface 39. Preformed members 136 and 138 may be formed from materials listed previously for forming an optical coupling member and are sized to form a press fit or interference fit between the respective photonic surfaces of the opto-electronic devices and corresponding lens inner surfaces as shown in FIG. 5B.

Figure 6:
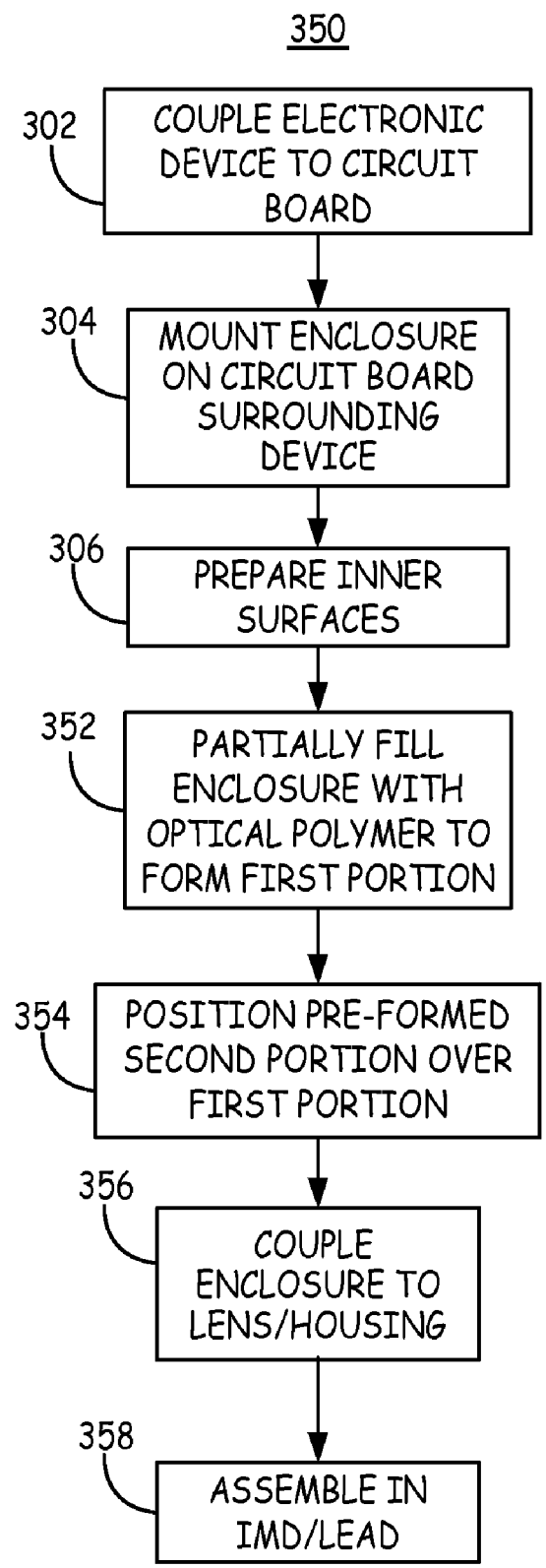
FIG. 6 is a flow chart of one method for manufacturing an optical sensor having a two-part optical coupling member.

FIG. 6 is a flow chart of one method for manufacturing an optical sensor having a two-part optical coupling member. Blocks 302 through 306 correspond to identically-numbered blocks described previously in conjunction with FIG. 2. At block 352, the enclosure is partially filled with an optical polymer material to form a first optical coupling portion over the opto-electronic device mounted on the circuit board. After curing the first optical coupling member, a pre-formed second coupling member portion is positioned over the first optical coupling member at block 354. Alternatively, an optical gel is deposited over the first optical coupling member. The enclosure is coupled to the lens at block 356, for example using a ferrule as described previously. Upon coupling the enclosure to the lens, the second coupling member forms an interference or compression fit between the lens and the first coupling member to thereby minimize reflections that otherwise occur at the lens inner surface and at the opto-electronic device surface.

At block 358, the sensor is assembled in an IMD or medical electrical lead for use as an implantable optical sensor as described previously in conjunction with FIG. 2.

Figure 7A:
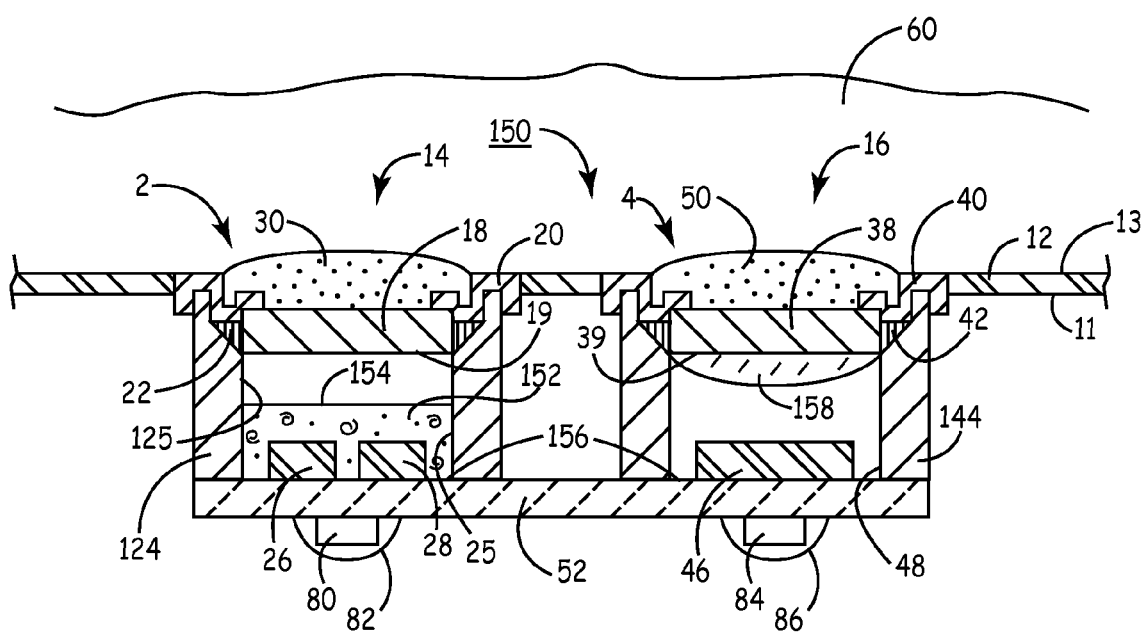
FIG. 7A is a side sectional view of an optical sensor including optical coupling members formed according to an alternative embodiment of the invention.

FIG. 7A is a side sectional view of an optical sensor including optical coupling members formed according to an alternative embodiment of the invention. As in previous drawings, components included in sensor 150 correspond to like-numbered components shown in FIG. 1. Sensor 150 includes a light emitting portion 14 having an optical coupling member 152 formed by partially filling enclosure 124 surrounding LEDs 26 and 28 with an optical polymer having a high index of refraction, for example approximately 1.5 or greater. Member 152 will increase the efficiency of light extraction from LEDs 26 and 28 compared to the light extraction that occurs when the LEDs 26 and 28 interface with air. However, light leaving member 152 at photonic surface 154 may be reflected at inner surface 19 of lens 18. In order to increase the percentage of light emitted by LEDs 26 and 28 that actually leaves light emitting portion 14 and passes through window 2, inner surfaces of light emitting portion 14, not including surfaces in window 2, may be formed as highly reflective surfaces. In one embodiment, enclosure 124 is fabricated from a highly reflective material, such as a white polymeric material or a polished metallic material. Alternatively, inner surface 125 of enclosure 124 is provided with a reflective coating. The material or coating is generally desired to be greater than 50% reflective. Suitable materials for forming a reflective enclosure include white liquid crystal polymer, such as Zenite 6130L WT010 available from Dupont, Spectralon®, available from Labsphere (North Sutton, N.H.), or GORE™ DRP®, available from W.L. Gore & Associates, (Newark, Del.). Suitable coatings may include white paint, metallic coatings such as gold or silver, Spectraflect® (available from Labsphere, North Sutton, N.H.), or titanium dioxide (TiO2). Circuit board 52 may also be formed of a reflective material or provided with a reflective coating on top surface 156. Circuit board 52 may be provided as a white circuit board, a Teflon coated circuit board (available from IMI, Incorporated, Haverhill, Mass.), or coated with a white paint, metallic coating, or Spectraflect.

Light detecting portion 16 includes an optical coupling member 158 formed on the inner surface 39 of lens 38. Optical coupling member 158 is formed by depositing an optical polymer having a refractive index selected to reduce reflections at inner surface 39. The optimal refractive index of coupling member 158 is the square root of the product of the refractive index of lens 38 and the refractive index of air. When lens 38 is formed from sapphire with a refractive index of about 1.7, the optimal refractive index of member 158 is about 1.3. While the optimal index is 1.3, commercially available materials may be limited to about 1.4. Three example materials include EG-6301 and OE-6336 available from Dow Corning, and OPT 7020 available from Intertronics (Oxfordshire, England). By providing optical coupling member 158 having an optimized refractive index along lens 38, light scattered by body fluid/tissue volume 60 will pass through window 4 with less reflection occurring at the lens inner surface 39 than if the lens inner surface 39 interfaces with air. As in light emitting portion 14, enclosure 144 and circuit board 52 may be fabricated from highly reflective materials or enclosure inner surface 48 and circuit board top surface 156 may be provided with reflective coatings. Highly reflective inner surfaces of light detecting portion 16 will increase the percentage of light entering light detecting portion 16 that actually reaches photodetector 46.

Figure 7B:
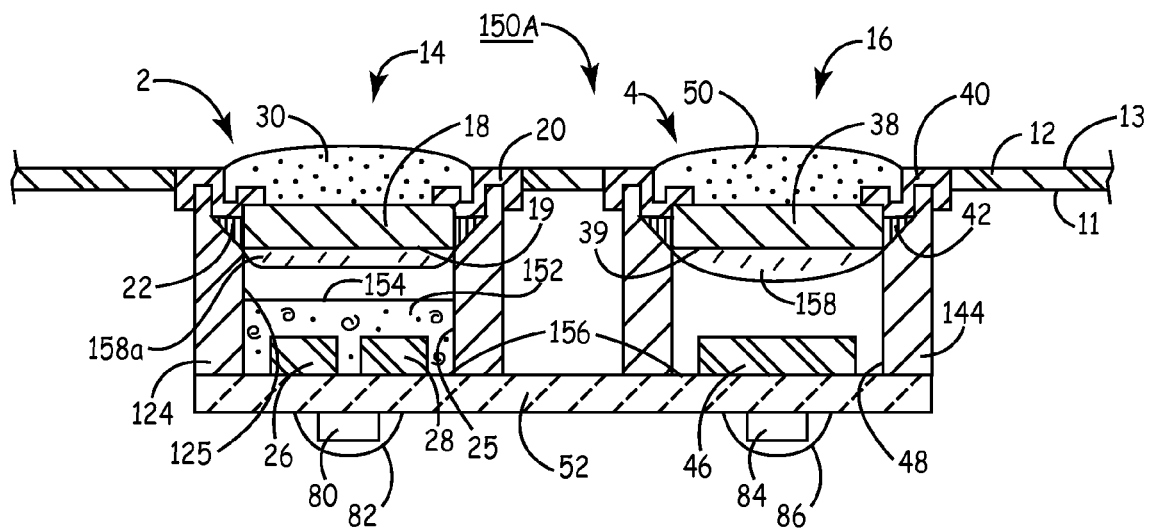
FIG. 7B is a side sectional view of an optical sensor that includes a first optical coupling member formed by partially filling an enclosure and a second optical coupling member formed on inner surface of a window lens.

It is recognized that in some embodiments, an optical coupling member may be formed over a lens inner surface and another optical coupling member may be formed to embed photonic surfaces of light emitting or detecting devices. FIG. 7B is a side sectional view of an optical sensor 150a that includes a first optical coupling member 152 formed by partially filling enclosure 124 and a second optical coupling member 158a formed on inner surface 19 of lens 18 in emitting portion 14. First optical coupling member 152 is provided with a high refractive index to reduce light reflections at photonic surfaces of LEDs 26 and 28. Second optical coupling member 158a is formed from a material having a refractive index selected to reduce reflection of light at lens inner surface 19.

Figure 8:
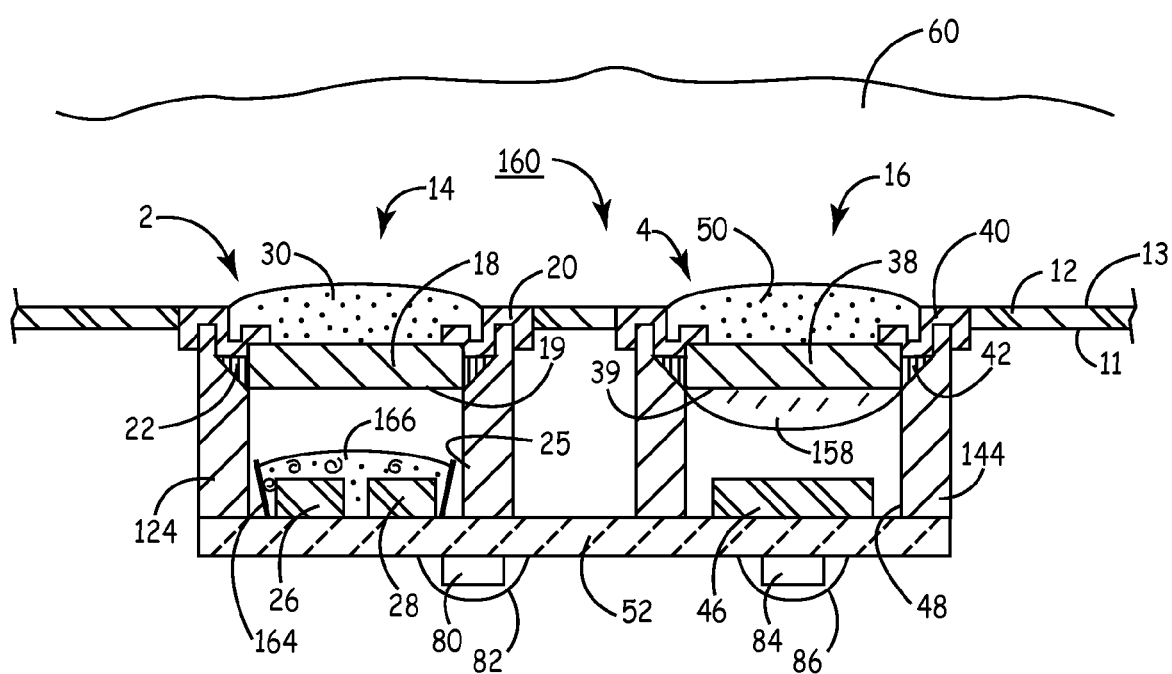
FIG. 8 is a side sectional view of an optical sensor having LEDs potted in an optical coupling member.

FIG. 8 is a side sectional view of an optical sensor 160 having LEDs potted in an optical coupling member. Rather than partially filling an enclosure 124 surrounding LEDs 26 and 28 as shown in FIG. 7A, LEDs 26 and 28 are shown in FIG. 8 positioned in a cup-shaped member 164 formed from a highly reflective material or having a highly reflective coating applied to its inner surface. Highly reflective materials and coatings listed above are also appropriate for fabricating cup-shaped member 164. Wire bonds (not shown) electrically couple the LEDs 26 and 28 to traces (not shown) formed on circuit board 52. Cup-shaped member 164 is filled with an optical polymer to form an optical coupling member 166 in which LEDs 26 and 28 become embedded. Cup-shaped member 164 is coupled to circuit board 52. Enclosure 124 and circuit board 52 may also be formed from highly reflective materials or provided with reflective coatings, as described above, to increase the percentage of light emitted from LEDs 26 and 28 that actually leaves emitting portion 14. Other components shown in sensor 160 correspond to like-numbered components shown in FIG. 7A.

Figure 9:
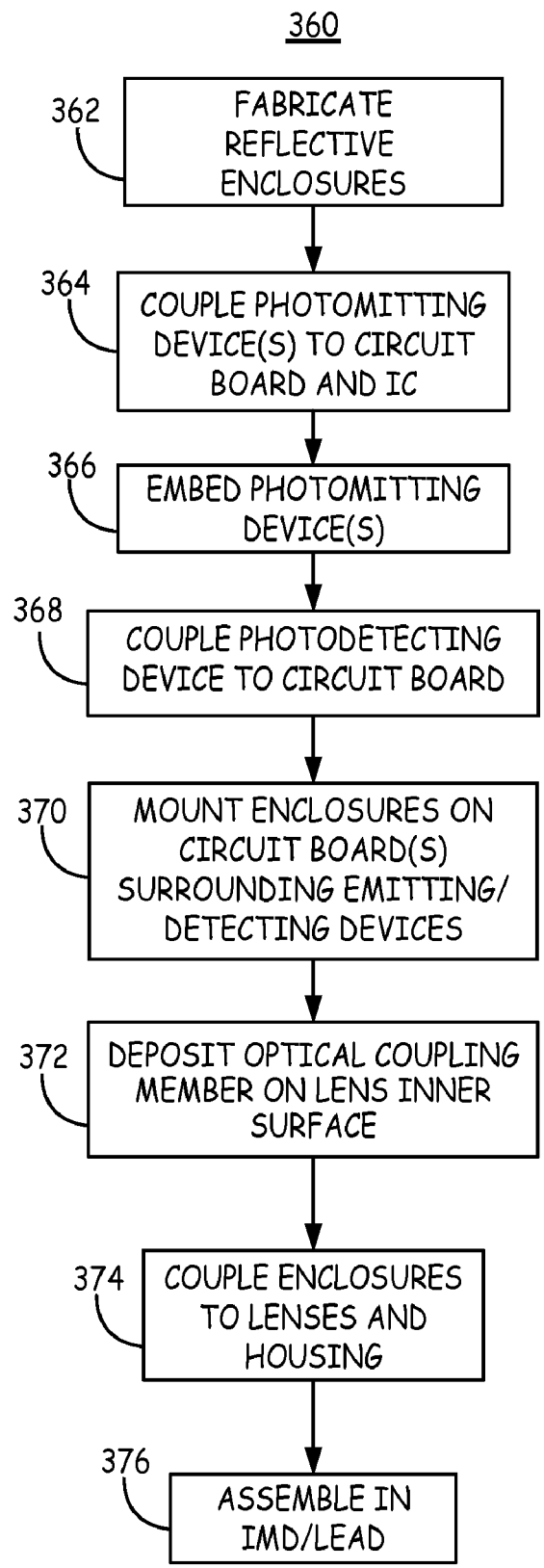
FIG. 9 is a flow chart of a manufacturing method for fabricating the optical sensors shown in FIG. 7A, 7B or 8.

FIG. 9 is a flow chart of a manufacturing method 360 for fabricating the optical sensors shown in FIG. 7A, 7B or 8. At block 362, reflective enclosures are fabricated for surrounding a light emitting portion and a light detecting portion of the optical sensor. The reflective enclosures may be formed from a reflective material or provided with a reflective coating on the inner surfaces of the enclosures. In each of the embodiments shown in FIGS. 7A through 8 air interfaces remain at component surfaces within the optical sensor making the use of reflective materials or coatings in forming the enclosures and/or circuit boards more important in improving the optical efficiency of the sensor than in previously presented embodiments in which air-component interfaces were eliminated within the sensor.

At block 364, one or more photoemitting devices included in a light emitting portion are coupled to the circuit board and electrically coupled to integrated circuitry used for providing driver signals to the photoemitting devices. The circuit board is fabricated from a reflective material or is provided with a reflective coating as described above. With regard to the embodiment shown in FIG. 8, the photoemitting device(s) are first positioned in a cup-shaped member which is then coupled to the circuit board.

At block 366, the photoemitting device(s) are embedded in an optical polymer. Embedding the photoemitting device(s) may involve partially filling an enclosure surrounding the emitting device as shown in FIG. 7A and as generally described in conjunction with FIG. 6. Alternatively, embedding the photoemitting device(s) may involve positioning the devices in a cup-shaped member and filling the cup-shaped member with an optical polymer material as shown in FIG. 8.

At block 368, a photodetecting device is coupled to a circuit board, which may be a circuit board shared with the photoemitting device(s) or a separate circuit board. The circuit board is fabricated from a reflective material or is provided with a reflective coating as described above. At block 370, the reflective enclosures are mounted on the circuit board (s), surrounding the photodetecting device and the photoemitting devices. It is recognized that the enclosure surrounding the photoemitting device(s) is positioned prior to embedding the photoemitting device(s) for the embodiments shown in FIG. 7A and 7B.

At block 372, an optical coupling member is deposited on the inner surface of the detecting portion lens. An optical coupling member may optionally be deposited on the inner surface of the emitting portion lens. The optical coupling member may be a preformed member that is bonded to the lens using a polymer adhesive. Alternatively, the optical coupling member may be formed by applying a bolus of an uncured optical polymer material to the lens surface and allowing it to cure.

After forming the optical coupling member on the lens inner surface(s), the enclosures are coupled to the lenses and sensor housing thereby forming the light emitting portion and the light detecting portion of the sensor. At block 376 the sensor is assembled in an IMD or lead for use as an implantable optical sensor as described previously.

Figure 10:
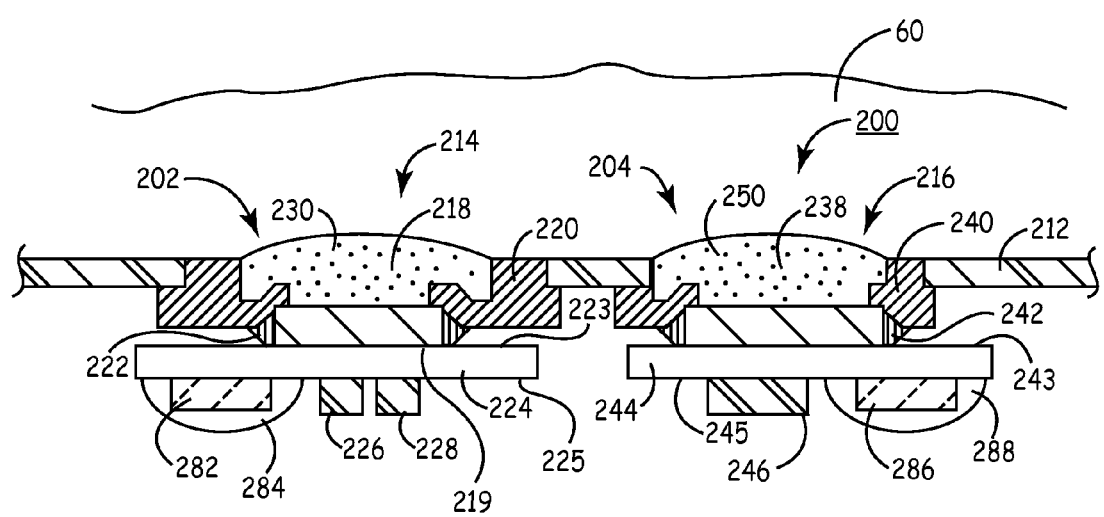
FIG. 10 is a side sectional view of an optical sensor including an optical substrate which additionally serves as an optical coupling member.

FIG. 10 is a side sectional view of an optical sensor including an optical substrate which additionally serves as an optical coupling member. Sensor 200 includes a light emitting portion 214 and light detecting portion 216. Light emitting portion 214 includes optical substrate 224 having a top surface 223 and a bottom surface 225. Optical substrate 224 may be formed from sapphire, glass or a rigid, optical polymer. LEDs 226 and 228 are mounted on substrate bottom surface 225 with the photonic surface attached to the substrate bottom surface 225. An optical polymer may be used to backfill between the photonic surfaces of the LEDs 226 and 228 and the substrate 224. LEDs 226 and 228 may be provided as flip chip LEDs electrically coupled to integrated circuitry 282 by bump bonding to electrical traces printed on substrate 224. Alternatively, the LEDs 226 and 228 may be fabricated directly onto substrate 224 using wafer scale deposition processes. In other embodiments, through wafer vias may be formed in LEDs 226 and 228 and the LEDs may then be electrically coupled to traces printed on substrate 224 using wire bonds. After coupling LEDs 226 and 228 to integrated circuit 282, a hard dye coating 284 is applied over integrated circuit 282.

Window 202 includes lens 218 coupled to ferrule 220 by gold braze joint 222. Seal 230 may be formed over ferrule 220 and lens 218. Ferrule 220 is welded or otherwise joined to sensor housing 212. The top surface 223 of substrate 224 is bonded to the inner surface 219 of lens 218. Bonding of substrate 224 to lens 218 may be achieved using an optical polymer or using a covalent bonding process. Light emitted by LEDs 226 and 228 travel through substrate 224 and window 202 to adjacent body fluid/tissue volume 60. In some embodiments, lens 218 and substrate 224 are made of the same material or two different materials having the same or similar refractive index.

In light detecting portion 216, photodetector 246 is mounted on the bottom surface 245 of an optical substrate 244 with the photonic surface of photodetector 246 against bottom surface 245. Photodetector 246 is electrically coupled to integrated circuit 286, embedded in hard dye coating 288, using any of the methods listed above with regard to emitting portion 214. Window 204 includes lens 238 coupled to ferrule 240 by gold braze joint 242. Seal 250 may be formed over ferrule 240 and lens 238. Ferrule 240 is welded or otherwise joined to sensor housing 212. The top surface 243 of substrate 244 is bonded to lens 238 such that light scattered by body fluid/tissue volume 60 travels through seal 250 and lens 238 (forming window 204) and substrate 244 to photodetector 246. In some embodiments, lens 238 and substrate 244 are made of the same material or two different materials having the same or similar refractive index.

Figure 11:
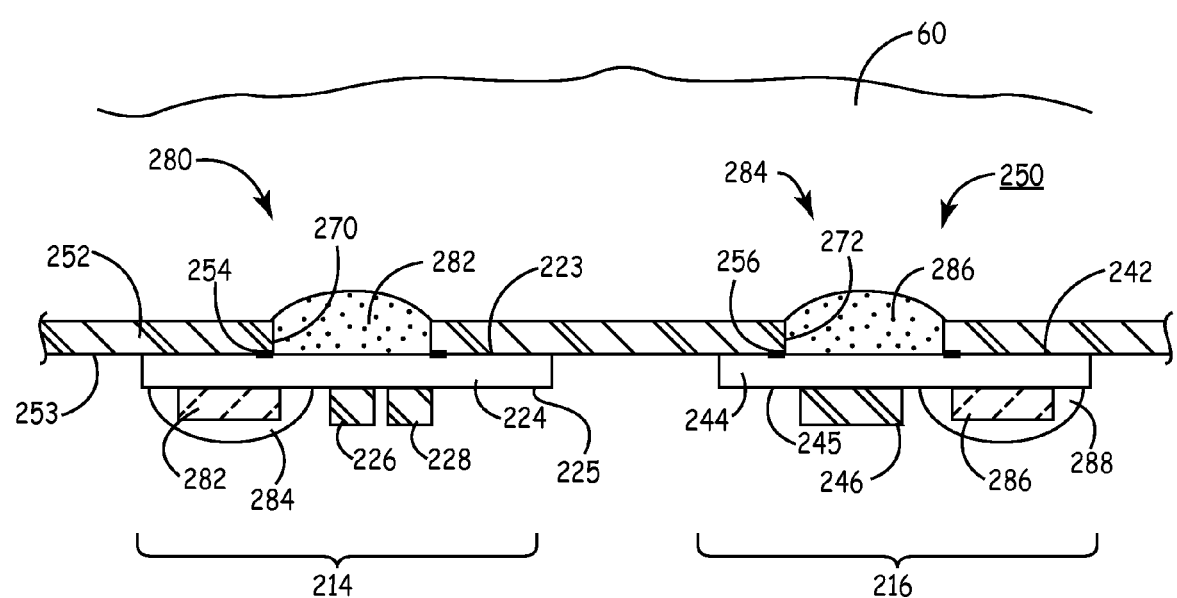
FIG. 11 is a side sectional view of yet another embodiment of an optical sensor having an optical substrate serving additionally as an optical coupling member.

FIG. 11 is a side sectional view of yet another embodiment of an optical sensor having an optical substrate serving additionally as an optical coupling member. In FIG. 11, components correspond to like-numbered components shown in FIG. 10. In sensor 250, window 280 is formed as an opening 270 in housing 252. Substrate 224, having LEDs 226 and 228 mounted thereon, is mounted directly to an inner surface 253 of sensor housing 252. Window 280 includes a sealing member 282 formed over optical substrate top surface 223 in opening 270. Methods used to electrically couple LEDs 226 and 228 to integrated circuitry 282 correspond to those described above. Substrate 224 may be mounted on housing inner surface 253 by a gold braze joint 254. In one embodiment, a Niobium ring is printed on the substrate top surface 223. A gold ring is melted onto the Niobium ring to form an intermetallic complex. The substrate is then coupled to the housing by localized laser heating through the substrate to braze the intermetallic ring to the housing. A gold ring may be deposited onto the housing to mate with the intermetallic ring and form joint 254 during the brazing procedure.

Similarly, photodetector 246 is mounted on a bottom surface 245 of optical substrate 244 in light detecting portion 216. Optical substrate 244 is mounted directly to housing inner surface 253. Window 284 is formed as an opening 272 in housing 252 and may include seal 286 formed over opening 272 and the underlying optical substrate top surface 243.

Figure 12:
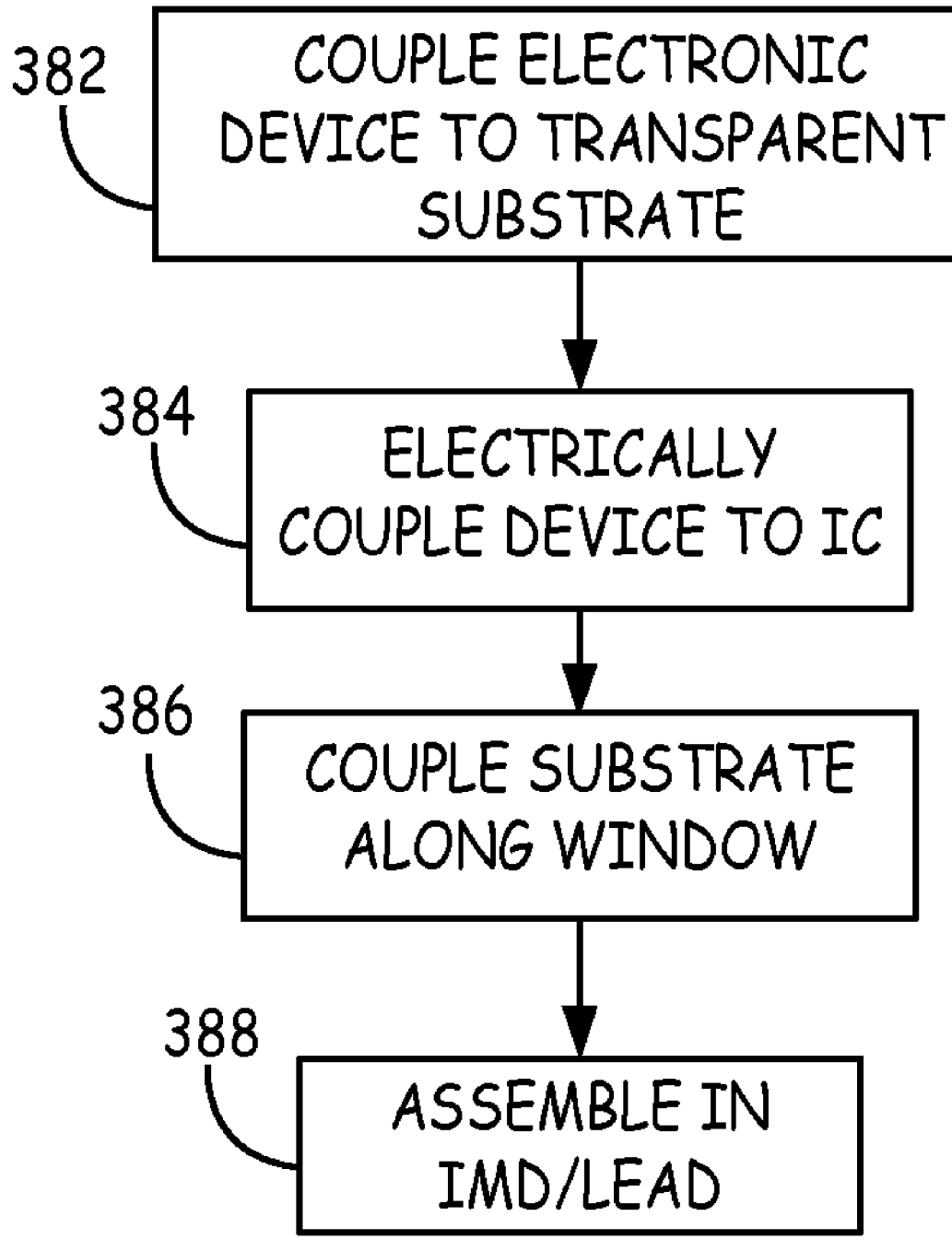
FIG. 12 is a flow chart summarizing a method for manufacturing an optical sensor including an optical substrate which additionally serves as an optical coupling member.

FIG. 12 is a flow chart summarizing a method 380 for manufacturing an optical sensor including an optical substrate which additionally serves as an optical coupling member. At block 382, an opto-electronic device for emitting light or for detecting light is coupled to a bottom side of an optical substrate. The device is electrically coupled to an integrated circuit, also mounted to the bottom side of the substrate at block 384. Electrical coupling may be achieved using bump bonding, wire bonding, wafer scale deposition methods, or other appropriate methods. At block 386, the substrate top surface is coupled along a window formed in an opening of the sensor housing such that the opto-electronic device is operatively aligned to transmit or receive light through the window and the optical substrate. The substrate top surface is coupled to a window lens as shown in FIG. 10 or directly to the sensor housing as shown in FIG. 11 using coupling methods described previously. At block 388, the sensor is assembled in an IMD or medical electrical lead for use as an implantable optical sensor.

Figure 13:
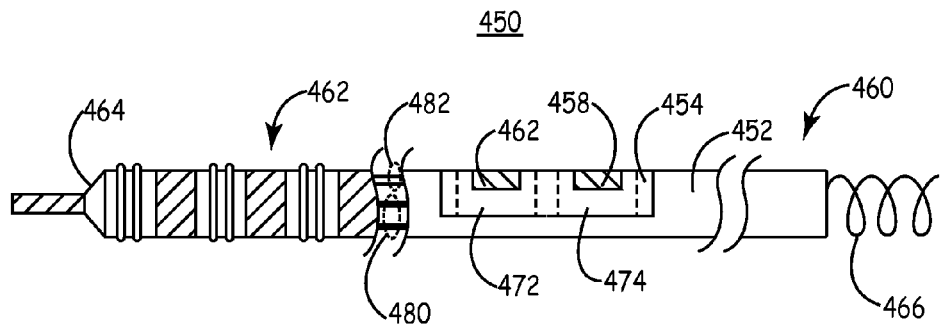
FIG. 13 is a plan view of a medical lead including an optical sensor according to one embodiment of the invention.

FIG. 13 is a plan view of a medical lead including an optical sensor according to one embodiment of the invention. Lead 450 includes an elongated body 452 extending between a proximal end 462 and a distal end 460. A sensor 454 is positioned along lead body 452, typically near distal end 460. Sensor 454 includes at least two windows 456 and 458 through which emitted light and scattered light travels from/to an emitting portion 472 and a detecting portion 474, respectively, of sensor 454.

Lead body 454 carries separately insulated conductor pairs 480 and 482 between a proximal connector assembly 464 and sensor 454. Conductor pair 480 is provided for carrying drive signals from proximal connector assembly 464 to LEDs via integrated circuitry in emitting portion 472. Conductor pair 482 is provided for carrying current generated by a photodetector included in detecting portion 474 to proximal connector assembly 464. Connector assembly 464 is coupled to an implantable medical device to thereby couple the sensor 454 to a sensor module included in the medical device. The sensor module includes sensor driver circuitry and signal processing circuitry (not shown in FIG. 13).

Lead 450 is shown having a distal fixation member 466 for anchoring the position of distal end 460 at a targeted implant location. In some embodiments, fixation member 466 may serve as an electrode and be coupled to an insulated conductor extending to proximal connector assembly 464. In various embodiments lead 450 may include other sensors and/or electrodes. As such, it is recognized that the particular configurations of lead body 452, conductors carried by the lead body and the proximal connector assembly 464 will depend on the particular configuration of electrodes and sensors carried by lead 450. Lead 450 may also include an open lumen, for example for use in delivering a fluid agent or passing a guide wire.

Figure 14:
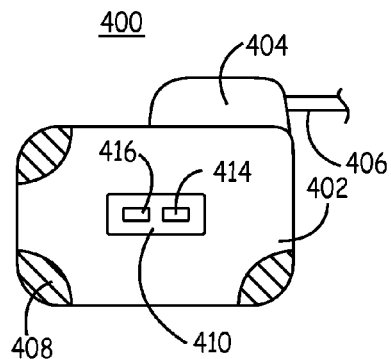
FIG. 14 is a plan view of an IMD in which an optical sensor is incorporated in the housing of the IMD.

FIG. 14 is a plan view of an IMD 400 in which an optical sensor 410 is incorporated in the housing 402 of device 400.

IMD 400 includes hermetically sealed housing 402, a connector block 404 and may include an electrode array 408 or other physiological sensors incorporated in housing 402. Sensor 410 is hermetically sealed within an opening in IMD housing 402 such that windows 414 and 416 associated with light emitting and light detecting portions of sensor 410 are exposed to adjacent tissue or body fluid when the IMD 400 is implanted in a subcutaneous, submuscular or other internal body location. While windows 414 and 416 are shown generally quadratic in shape, it is recognized that windows 414 and 416 may have alternative shapes, for example generally circular or oval. Electrical connections (not shown) between sensor 410 and IMD circuitry (not shown) enclosed in housing 402 allow the sensing function of sensor 410 to be controlled by IMD 400 and signal processing of signals responsive to detected light to be performed by IMD 400.

Lead 406 is shown coupled to connector block 404 allowing any electrodes or sensors carried by lead 406 to be electrically coupled to circuitry enclosed within housing 402. Lead 406 may correspond to lead 450 shown in FIG. 13 such that a lead-based optical sensor can be coupled to IMD 400. It is recognized that in alternative embodiments, IMD 400 may be provided as a leadless device, without connector block 400, including only sensors/electrodes incorporated in housing 402. IMD 400 may be embodied as a monitoring-only device or may include therapy delivery capabilities, such as electrical stimulation or drug delivery capabilities, responsive to signals generated by sensor 410.

Figure 15:
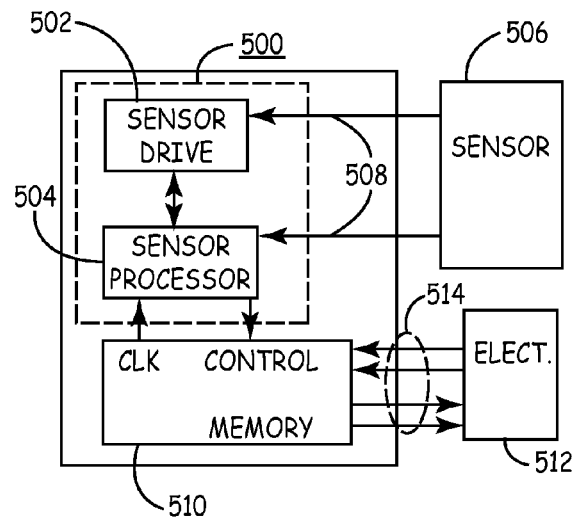
FIG. 15 is a functional block diagram of circuitry included in an IMD system that includes an optical sensor.

FIG. 15 is a functional block diagram of circuitry included in an IMD system that includes an optical sensor. Sensor module 500 includes a sensor driver circuit 502 and sensor processor circuit 504. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality. Conductor elements 508 extending from an optical sensor 506, which may correspond to any of the sensor embodiments described herein or variations thereof, provide connection to sensor driver circuit 502 and sensor processor circuit 504 via any necessary connector elements, feedthroughs, etc. Sensor driver circuit 502 provides the operational power for optical sensor 506 and controls the timing of optical sensor operation. Sensor processor circuit 504 receives optical sensor signal output and processes the signal output to estimate a change in a physiological condition, such as blood oxygen saturation, glucose saturation, tissue perfusion or any other physiological condition causing alterations in light modulation by the measurement body fluid or tissue volume. Sensor driver circuit 502 and sensor processor circuit 504 may operate as generally disclosed in U.S. Pat. No. 4,730,389 (Baudino et al.), hereby incorporated herein by reference in its entirety.

Operation of sensor module 500 is controlled by control module 510 which may include a microprocessor and associated memory, a clock signal (CLK) and power supply. Control module 510 controls other device functions, including data storage and other sensing and/or therapy delivery functions, which may be performed in conjunction with electrodes 512 coupled to control module 510 via conductors 514. Detailed descriptions of such circuitry included in an implantable medical device and its operation are provided in the above-incorporated '952 patent to Miesel.

Thus, an implantable optical sensor including an optical coupling member for use in implantable medical device systems has been presented in the foregoing description with reference to specific embodiments. It is appreciated that various modifications to the referenced embodiments may be made without departing from the scope of the invention as set forth in the following claims.

The invention claimed is:

1. An implantable medical device, comprising:
  a housing having an inner surface and an outer surface;
  a window formed in the housing extending between the housing inner surface and the housing outer surface;
  an optical lens mounted in the window to maintain hermeticity of the device;
  an opto-electronic device enclosed within the housing and having a photonic surface operatively positioned proximate the window for one of emitting light through the window and detecting light through the window, the housing and the lens enclosing an interior space between the lens and the opto-electronic device; and
  a first optical coupling member filling the interior space between the opto-electronic device and the lens to reduce light reflection at a surface within the implantable medical device.

2. The implantable medical device of claim 1 wherein the first optical coupling member comprises an optical substrate, the opto-electronic device being mounted on the substrate.

3. The implantable medical device of claim 2 wherein the substrate is coupled to the housing inner surface along the window.

4. The implantable medical device of claim 2 wherein the optical lens is coupled to the housing, the lens having an inner surface, and wherein the substrate is coupled to the lens inner surface.

5. The implantable medical device of claim 1 wherein the optical lens is coupled to the housing, the lens having an inner surface, and wherein the first optical coupling member is coupled to the lens inner surface to reduce light reflection at the lens inner surface.

6. The implantable medical device of claim 1 further comprising:
  a substrate, the opto-electronic device mounted on the substrate; and
  an enclosure surrounding the opto-electronic device and coupled to the substrate, the enclosure extending from the substrate to the window, wherein the first optical coupling member comprises an optical material filling at least a portion of the enclosure and embedding the photonic surface of the opto-electronic device to reduce reflection of light at the photonic surface.

7. The implantable medical device of claim 6 wherein the substrate includes a port through which the material is introduced into the enclosure.

8. The implantable medical device of claim 6 wherein the first optical coupling member is a pre-formed member.

9. The implantable medical device of claim 6 wherein the optical material has a first coefficient of thermal expansion and the enclosure has a second coefficient of thermal expansion greater than the first coefficient of thermal expansion, and wherein the optical material is compressed within the enclosure after cooling the enclosure and the optical material from a temperature corresponding to a curing temperature of the optical material.

10. The implantable medical device of claim 9 wherein the medical device further comprises a pressure relief member to receive a portion of the compressed material.

11. The implantable medical device of claim 6 further comprising a second optical coupling member positioned between the first optical coupling member and the window, wherein the lens is coupled to the housing and having an inner surface, and wherein the second optical coupling member reduces light reflection at the lens inner surface.

12. The implantable medical device of claim 11, wherein the second optical coupling member has a first durometer and the first optical coupling member has a second durometer greater than the first durometer, the second optical coupling member forming an interference fit between the lens and the first optical coupling member.

13. The implantable medical device of claim 11 wherein the second optical coupling member is one of a preformed member and an optical gel.

14. The implantable medical device of claim 11 wherein the index of refraction of the second optical coupling member approximately matches the index of refraction of the first optical coupling member.

15. The implantable medical device of claim 11 wherein the second optical coupling member is coupled to the lens inner surface, the second optical coupling member has an inner surface separated from the first optical coupling member, the first optical coupling member has a first index of refraction and the second optical coupling member has a second index of refraction lower than the first index of refraction.

16. The implantable medical device of claim 1 wherein the first optical coupling member comprises a cup-shaped member and an optical material filling the cup-shaped member, the photonic surface being embedded within the optical material for reducing light reflection at the photonic surface.

17. The implantable medical device of claim 1 further comprising
the lens having an inner and outer surface; and
a seal formed over the lens outer surface, wherein the seal is formed from an optical polymer having an index of refraction selected to reduce reflection of light at the lens outer surface.

18. The implantable medical device of claim 1 further comprising conductors extending from the opto-electronic device, wherein the conductors are insulated from the housing inner surface by the optical coupling member.

19. The implantable medical device of claim 18 wherein the photonic surface is approximately 15 mils or less from the housing inner surface.

20. An implantable medical device, comprising:
a housing;
a light emitting portion comprising a first window formed in the housing, a first lens mounted in the window to maintain hermeticity of the housing, and a light emitting device operatively positioned within the housing for transmitting light through the first window, the housing and the first lens enclosing a first interior space between the first lens and the light emitting device;
a light detecting portion comprising a second window formed in the housing, a second lens mounted in the window to maintain hermeticity of the housing, and a light detecting device operatively positioned within the housing for receiving light transmitted through the second window, the housing and the second lens enclosing a second interior space between the second lens and the light detecting device; and
means filling at least one of the first interior space and the second interior space for reducing light reflection occurring at a surface within the at least one of the first interior space and the second interior space as compared to light reflection occurring at the surface when the surface is interfaced with air.

21. A method for manufacturing an implantable optical sensor, comprising:
enclosing an opto-electronic device within a housing having an inner surface and an outer surface, the opto-electronic device having a photonic surface and being positioned in operative relation to a window extending between the housing inner surface and the housing outer surface, the opto-electronic device configured for one of emitting light and detecting light through the window;
mounting an optical lens in the window to maintain hermeticity of the housing; and
positioning a first optical coupling member between the opto-electronic device and the window to fill an interior space enclosed by the housing and the lens to reduce light reflection at a surface within the implantable optical sensor.

22. The method of claim 21 wherein the first optical coupling member comprises an optical substrate and further comprising mounting the opto-electronic device on the optical substrate.

23. The method of claim 22 further comprising coupling the optical substrate to the housing inner surface.

24. The method of claim 22, further comprising coupling the optical lens to the housing, the lens having an inner surface, and coupling the optical substrate to the lens inner surface.

25. The method of claim 21, further comprising coupling optical lens to the housing, the lens having an inner surface, and coupling the first optical coupling member to the lens inner surface to reduce light reflection at the lens inner surface.

26. The method of claim 21 wherein the first optical coupling member is a preformed member.

27. The method of claim 21 further comprising:
mounting the opto-electronic device on a substrate;
coupling an enclosure to the substrate, the enclosure surrounding the opto-electronic device and extending from the substrate to the window; and
filling at least a portion of the enclosure with a material for forming the first optical coupling member, the material embedding the photonic surface of the opto-electronic device to reduce light reflection at the photonic surface.

28. The method of claim 27 wherein filling at least a portion of the enclosure includes introducing the material through a port in the substrate.

29. The method of claim 27 further comprising:
heating the enclosure and the material to a temperature corresponding to a curing temperature of the material; and
cooling the enclosure and the material from the temperature,
wherein the material has a first coefficient of thermal expansion and the enclosure has a second coefficient of thermal expansion greater than the first coefficient of thermal expansion such that the material becomes compressed within the enclosure upon cooling.

30. The method of claim 29 wherein the sensor comprises a pressure relief member to receive a portion of the compressed material.

31. The method of claim 27 further comprising positioning a second optical coupling member between the first optical coupling member and the window, wherein the optical lens is coupled to the housing, the optical lens having an inner surface, and wherein the second optical coupling member reduces light reflection at the lens inner surface.

32. The method of claim 31 wherein the second optical coupling member has a first durometer and the first optical coupling member has a second durometer greater than the first durometer, the second optical coupling member forming an interference fit between the lens and the first optical coupling member.

33. The method of claim 31 wherein the second optical coupling member is one of a preformed member and an optical gel.

34. The method of claim 31 wherein the index of refraction of the second optical coupling member approximately matches the index of refraction of the first optical coupling member.

35. The method of claim 31 further comprising coupling the second optical coupling member to the lens inner surface, the second optical coupling member having an inner surface separated from the first optical coupling member, the first optical coupling member having a first index of refraction and the second optical coupling member having a second index of refraction lower than the first index of refraction.

36. The method of claim 21 wherein positioning the first optical coupling member comprises:

positioning the opto-electronic device in a cup-shaped member; and embedding the photonic surface of the opto-electronic device in an optical material by filling the cup-shaped member with the optical material.

37. The method of claim 21 wherein the lens having an outer surface and further comprising forming a seal over the lens outer surface, the seal formed of an optical polymer having an index of refraction selected to reduce light reflection at the lens outer surface.

38. The method of claim 21 wherein conductors extend from the opto-electronic device, and the first optical coupling member electrically insulates the conductors from the housing inner surface.

39. The method of claim 38 wherein the photonic surface is positioned approximately 15 mils or less from the housing inner surface.

* * * * *